US00PP14314P39

(12) United States Plant Patent

Nelson

(10) Patent No.: US PP14,314 P3
(45) Date of Patent: Nov. 25, 2003

(54) APPLE TREE NAMED 'LYNN'

(50) Latin Name: *Malus pumila, Mill.*
Varietal Denomination: Lynn

(76) Inventor: Billy A. Nelson, 21 Sunrise Ct., Rock Island, WA (US) 98850

( * ) Notice: Subject to any disclaimer, the term of this patent is extended or adjusted under 35 U.S.C. 154(b) by 31 days.

(21) Appl. No.: 10/118,689

(22) Filed: Apr. 8, 2002

(65) Prior Publication Data

US 2003/0192091 P1 Oct. 9, 2003

(51) Int. Cl.[7] ..... A01H 5/00
(52) U.S. Cl. ..... Plt./161
(58) Field of Search ..... Plt./161, 163

(56) References Cited

PUBLICATIONS

The Brooks and Olmo "Register of Fruit and Nut Varieties" 3rd edition, ASHA Press, 1997, p. 67.*
Web site, "Genetic Resource Inventory System", Internet, http://www.universaldbase.com, Feb. 1997.*

* cited by examiner

*Primary Examiner*—Bruce R. Campell
*Assistant Examiner*—Susan B. McCormick

(57) ABSTRACT

A new and distinct variety of apple tree, characterized by an unusually shiny yellow ground color and a glossy pink-red overcolor, maturing about 5 days later than 'Red Delicious', with crisp, juicy flesh capable of both dessert and culinary use.

4 Drawing Sheets

Latin name of the genus and species of the plant claimed: *Malus pumila*, Mill.
Variety denomination: 'LYNN'.

BACKGROUND OF THE INVENTION

Disclosed is a new and distinct variety of apple (*Malus pumila,* Mill) that was discovered in a cultivated area of the back yard of my residence off Washington State Highway 28, Rock Island, Wash. The seedling apparently germinated in about 1990 and was basically ignored until it fruited in 1999. I noticed the color and quality of this initial fruit. In the Spring of 2000, I grafted budwood from the seedling onto about 100 'Jonagold' (unpatented) trees growing on Malling 7 (unpatented) rootstock. This grafting took place in Rock Island, Wash. Approximately 10 of these grafts produced fruit in 2001. The fruit from these grafts and other characteristics of these grafts were identical to the fruit and other characteristics of the original seeding, thus confirming the stability of this new variety. I decided to call my new variety 'LYNN'.

BRIEF SUMMARY OF THE INVENTION

My new variety is a seedling apple tree with a distinct pink-red blush over about 20 to 80 percent of the fruit surface, which has a glossy yellow ground color. In addition, the fruit size typically is large, the shape conic, and the flesh crisp, juicy, and sweet-tart in flavor. These characteristics make it a clearly distinct new variety.

This apple of my new variety is very distinctive, not sharing a number of external or internal characteristics with any other variety. The apple of my new variety has the pink on yellow coloring similar to 'Winter Banana' (not patented), but is much different in shape. 'Winter Banana' is more round in shape with a very shallow basin. 'Winter Banana' apple ripens in mid-late October and 'Lynn' ripens in mid-September.

'Cripps Pink' (U.S. Plant Pat. No. 7,880) has a similar pinkish coloring but matures in late October to November and is much more acidic at harvest time.

'Blushing Golden' (U.S. Plant Pat No. 2,835) has a pinkish-red blush but resembles 'Golden Delicious' in shape and internal quality. The ground color of 'Blushing Golden' is deep yellow and dull in luster, while 'Lynn' is very glossy.

'Criterion' (U.S. Plant Pat. No. 3,505) is somewhat similar in color and maturity but very different in shape. 'Criterion' is distinctly conical and ribbed while 'Lynn' is more round conical with less prominent lobes at the calyx end. 'Criterion' is no longer grown commercially.

Asexual reproduction by grafting at Rock Island, Wash., as set forth above, has shown that the characteristics of my new variety are established, firmly fixed, and are transmitted through succeeding asexual propagation.

Certain characteristics of this variety, such as growth and color, may change with changing environmental conditions (e.g., photoperiod, temperature, moisture, soil conditions, nutrient availability, or other factors). Color descriptions and other terminology are used in accordance with their ordinary dictionary descriptions, unless the context clearly indicates otherwise. Color designations (hue/value/chroma) are made with reference to the Munsell Book of Color, Kollmorgen Instruments Corp., 405 Little Britain Road, New Windsor, N.Y. 12553.

BRIEF DESCRIPTION OF THE DRAWING

The accompanying color photographs (digital images) show typical tree, fruit, flower, and leaf Specimens of my new apple tree variety and depict the color as near to true as is reasonably possible to make the same in a color illustration of this character. It should be noted that colors may vary with growing conditions and time of year as well as with lighting conditions at the time the photographs are taken.

DETAILED BOTANICAL DESCRIPTION

Figure 1:
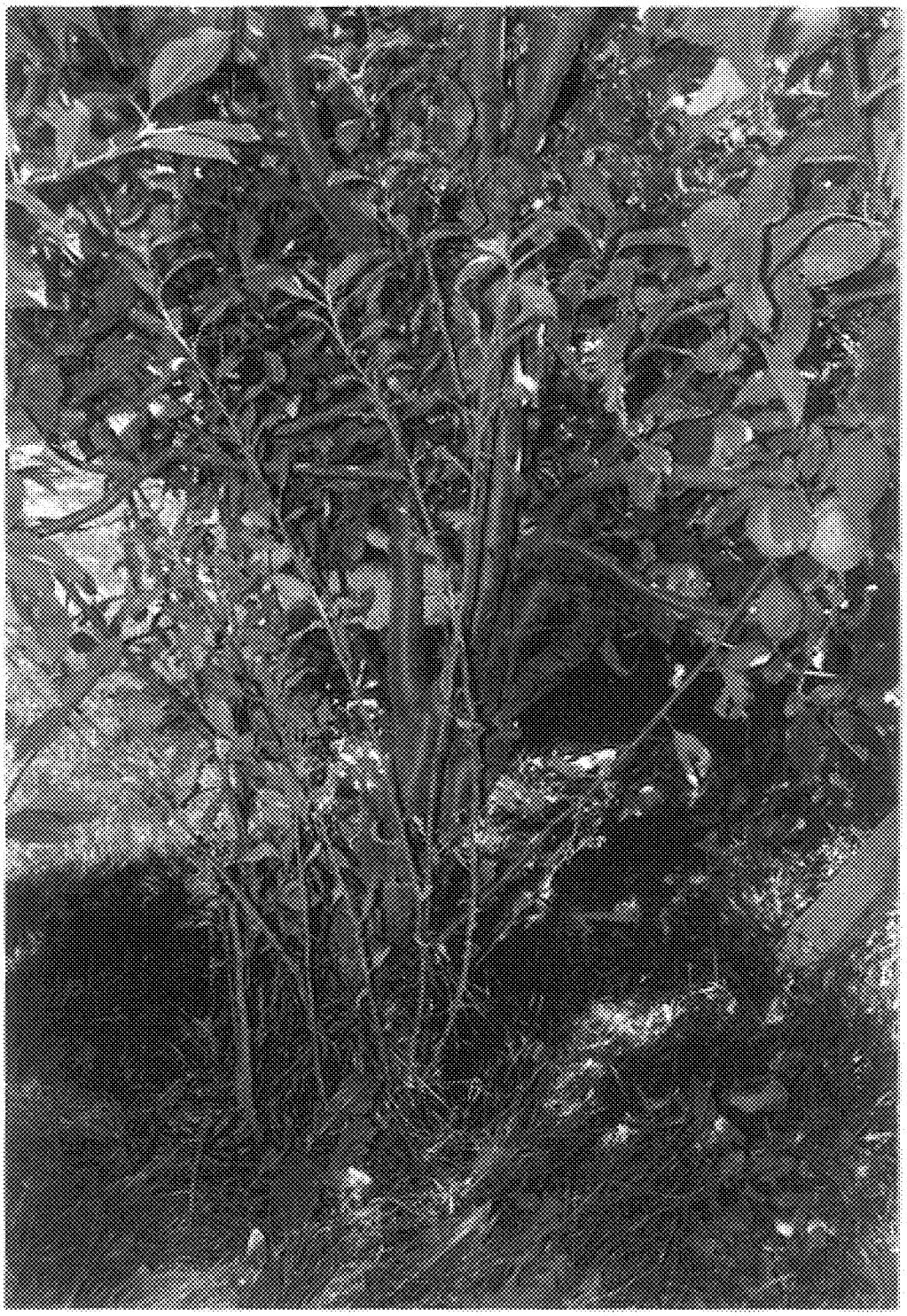
FIG. 1 is a photograph of the original tree of the 'Lynn' cultivar, showing multiple trunks, characteristic of a neglected seedling.
Figure 2:
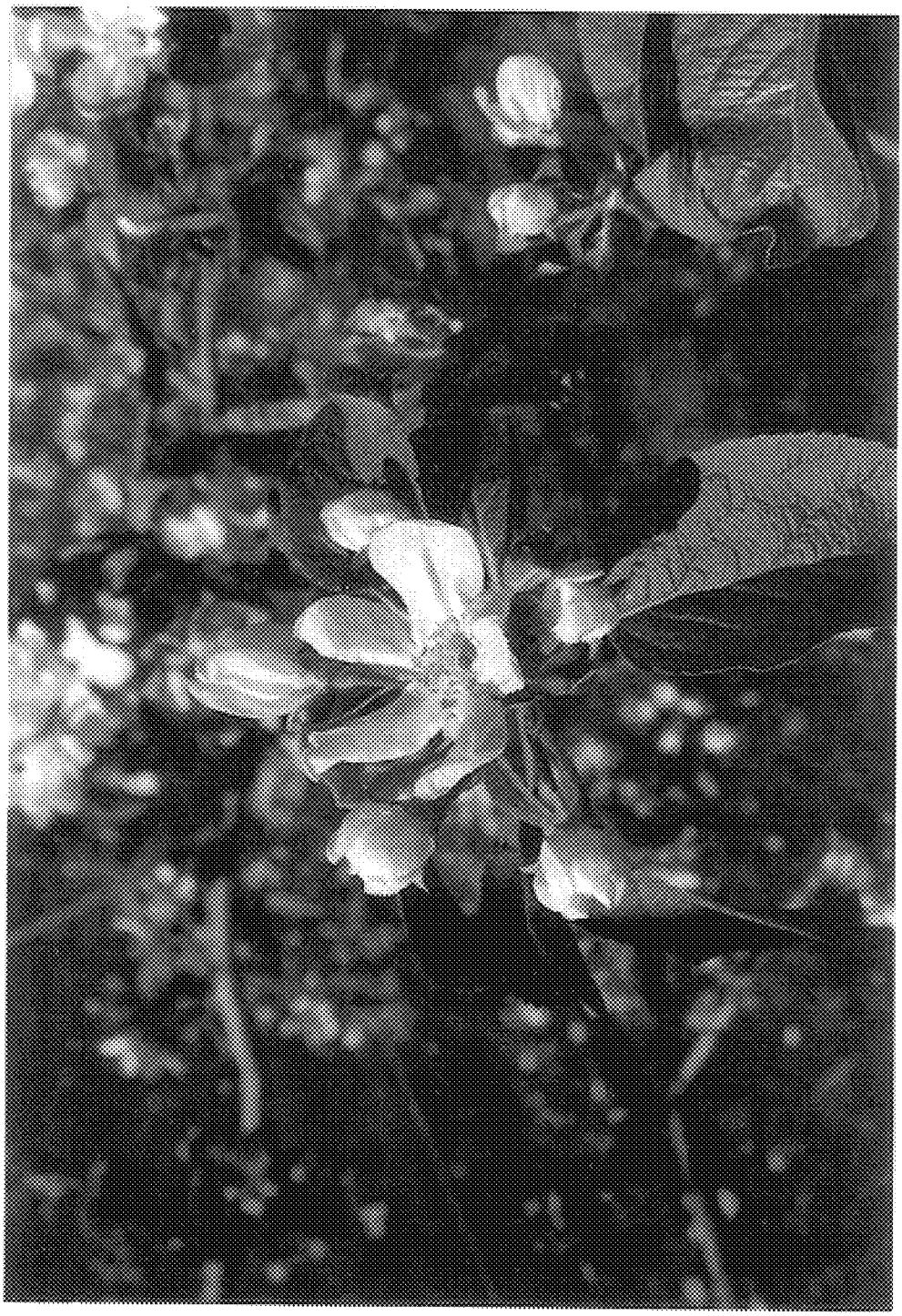
FIG. 2 is a photograph of the bloom of the 'Lynn' cultivar.
Figure 3:
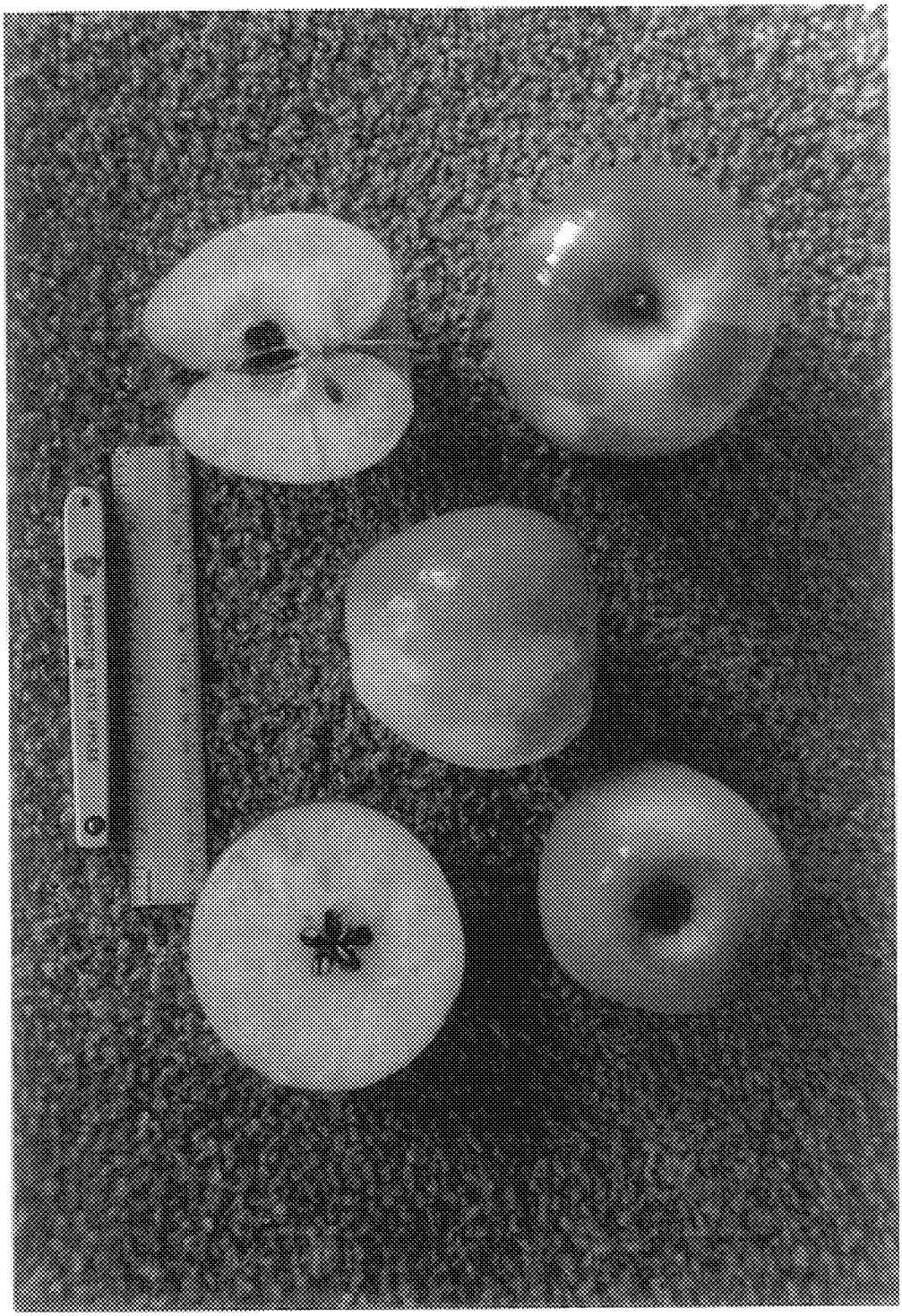
FIG. 3 is a photograph of the 'Lynn' cultivar fruit in various aspects.
Figure 4:
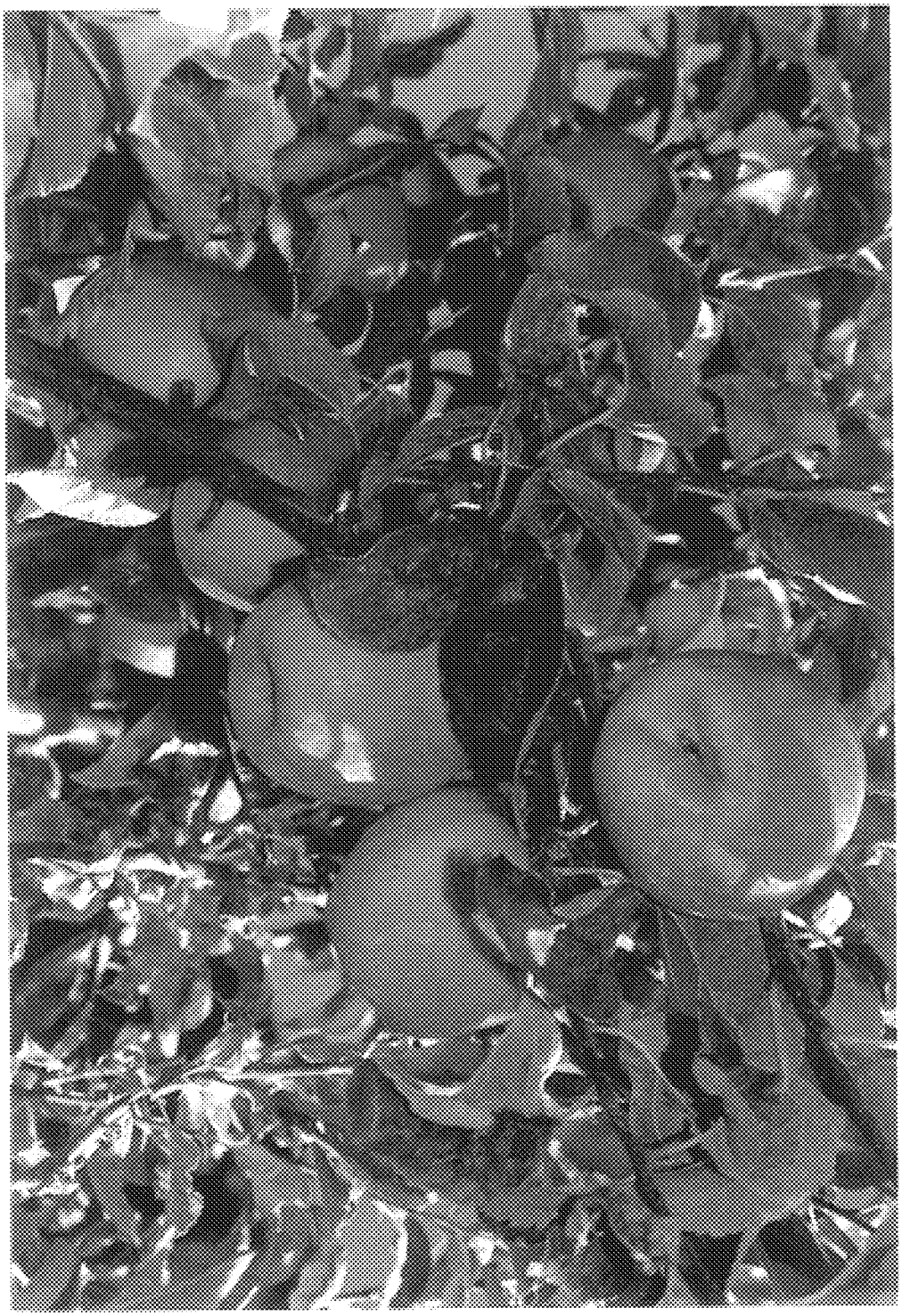
FIG. 4 is a photograph of leaves and fruit of the 'Lynn' cultivar.

The detailed description that follows is based on observations made of the original 'Lynn' cultivar tree growing in a cultivated area in Rock Island, Wash. This site is characteristic of orchard sites throughout north central Washington, near Wenatchee, Wash., where a wide variety of fruit, vegetable, and agronomic crops are grown under supplemental irrigation.

Scientific name: *Malus pumila,* Mill. 'Lynn'.
Origin: Seedling of unknown parentage.
Tree:
- *Vigor.*—Vigorous, annual growth of about 31 to 61 cm, averaging 47 cm, for the observed trees.
- *Height.*—Height of original tree at about 11 years of age, about 4 m, and about 2.5 m wide.
- *Habit.*—Upright, oblong shape.
- *Productivity.*—Moderately productive, annual bearing (based upon two years of observations).

Trunk:
- *Size* (*original tree*).—Stocky, about 24 cm in diameter at 30 cm from soil line, many suckers.
- *Bark texture.*—Smooth, becoming furrowed.
- *Bark color.*—Greenish yellow (5 Y 4/6).

Branches:
- *Habit.*—Upright to spreading, with fruiting branch angle at emergence about 30 to 60 degrees from horizontal.
- *Size and texture.*—Of medium size, with smooth texture in the immature tree, becoming rougher as tree wood matures. Two-year-old branches averaged 9 mm in diameter and 62 cm in length.
- *Color.*—Reddish brown (7.5 R 3/4), becoming greenish brown (5 Y 3/4) on older wood.

Pubescence: Sparse, becoming heavier at branch tip, colorless.
Lenticels: Medium in number, oblong shape, tan (7.5 R 8/2), about 0.5 mm wide by about 1 mm long.
Internodes: Average length on one-year-old shoots about 3.6 cm.
Leaves (based upon observation of ten leaves):
- *Size.*—Medium to large, from about 7 cm to 12 cm in length of leaf blade (averaging 8 cm) and about 4 cm to 10 cm in width (averaging 6 cm).
- *Sheen.*—Semi-glossy.
- *Petiole.*—About 2.5 to 4 cm long (averaging 3 cm); color: upper surface, pale gray green (10 GY 7/2), lower surface, light green (2.5 G 6/6).
- *Veins.*—Pale gray green, (10 GY 7/2).
- *Margin.*—Coarsely serrate on large leaves; finely serrate on small to medium leaves.
- *Tip.*—Acute to acuminate.
- *Stipules.*—Medium to large; about 7 to 15 mm in length, up to about 3 mm in width.
- *Color.*—Upwardly disposed surface, dark green (10 GY 4/4); downwardly disposed surface, medium green (10 GY 6/4); petiole, upper surface, pale gray green (10 GY 7/2), lower surface, light green (2.5 G 6/6).
- *Pubescence.*—Upper surface, lacking; lower surface, very fine, primarily on ribs; color tan/cream (2.5 Y 8.5/4).

Flowers (observations are from a sampling of typical flowers from original tree growing At Rock Island, Wash.):
Buds:
- *Size* (*popcorn stage*).—About 5.7 cm in length (including pedicel), with the bud alone measuring about 1.3 cm in length, by about 1.2 cm width.
- *Surface texture.*—Somewhat ridged and occasionally puckered on outside surface.
- *Color* (*popcorn stage*).—Pinkish purple (2.5 R 4/12).
- *Dates of bloom* (*Rock Island Wash.*), *2001.*—First bloom April 26; full bloom April 30 to May 2; petal fall May 10 to 13.
- *Petal number.*—5.
- *Size* (*fully open*).—Flower diameter about 5.3 cm.
- *Petals.*—About 29 mm long by about 13 mm wide, elongated oval.
- *Color.*—Pure white with slightly pink (2.5 R 9/2) veins on upper surface; lower surface pink (2.5 R 7/6) fading to white as flower ages.
- *Stamens.*—Arranged in a single row. About 18 stamens, each about 6 mm long.
- *Filaments.*—About 5 to 7 mm in length.
- *Anthers.*—Light yellow (5 Y 8.5/10).
- *Pistil.*—Five styles fused at base, about 7 mm long; stigma curving at distal end, round top.

Bloom fragrance: Almost imperceptible.
Showiness: Medium, typical of most apple flowers.
Sepals: Recurved downward, light green (2.5 GY 7/7), with fine, colorless pubescence; about 6 mm in length, about 4 mm wide at base.
Fertility: Diploid.
Pollination requirements: 'Lynn' is self infertile, but cross compatible with 'Red Delicious', 'Golden Delicious', 'Jonagold' and 'Gala' (all not patented). No incompatible pollinators have been found.
Pollen production: Abundant, but not exceptional.
Pollen color: Light yellow (5 GY 8.5/10).
Fruit (observations are from ten samples of typical fruit.):
- *Maturity when described.*—Mid-harvest period, Oct. 3, 2000 at Rock Island, Wash. Maturity of 'Lynn' is 5 days later than that of 'Red Delicious' (not patented). Firmness was 16 to 18 pounds (Taylor-Magness pressure tester); soluble solids (refractometer) was 13 to 14%; malic acid content (titration) was 0.75%; starch index (1–6 scale) was 3.5.
- *Size.*—Large, about 8 to 9 cm (3.25 to 3.5 inches); box size 56 to 80 (average of 10-fruit sample). Average weight 355 grams.
- *Form.*—Round conic, symmetric; length/diameter ratio approximately 1:1, with ribbing absent; slight crowning at distal end with inconspicuous lobes.
- *Stem cavity.*—Broad (about 40 to 50 mm), medium deep (about 22 to 26 mm), obtuse.
- *Basin cavity.*—Broad (about 30 to 35 mm), deep (about 12 to 17 mm).
- *Stem.*—Medium to short, average length 19 mm, width 2 mm; greenish (10 Y 6/6) with colorless pubescence.
- *Locules* (*carpels*).—Large, five in number, wide, open cluster.
- *Skin.*—Texture smooth; naturally glossy, but not greasy; not prone to russet; no tendency toward cracking observed to date; medium thickness.

*Lenticels.*—Greenish (2.5 6/6), sparse in concentration, inconspicuous, round, less than about 1 mm in diameter.

*General color effect.*—Bright pink-red blush, most apples 30 to 50% (tends to be less for apples within the interior of the tree, for example about 20% blush; tends to be greater for exposed apples, for example about 80% blush); unique color pattern of glossy red-pink over yellow, slightly similar in color to 'Winter Banana' (not patented) or 'Ozark Gold' (not patented).

*Ground color.*—5 Y 8.5/6 (yellow), stable throughout harvest period; slightly greener at early harvest.

*Overcolor.*—2.5 R 5/12 (pink blush).

*Russet.*—None observed to date.

*Flesh.*—Color, cream (7.5 Y 9/4).

*Texture.*—Crisp and juicy, somewhat melting after long storage.

*Flavor.*—Sprightly, subacid to acidic, somewhat similar to 'Cripps Pink' (U.S. Plant Pat. No. 7,880).

*Acidity.*—Moderate to high at harvest, up to 0.85%, decreasing with storage.

*Aroma.*—None

*Core.*—Round, small, about 24 mm width by about 20 mm length; number of bundles, 10; core lines sharply defined; core open; calyx tube short, typically closed.

*Seed.*—Obovate, usually 2 per cell, brown (10 YR 3/6); length about 9 mm, width about 4 mm, with loose adherence to carpel wall.

*Keeping quality.*—Good; fruit remains firm and crisp for about 2 weeks at room temperature.

*Storage.*—Up to 4 months in common storage, 6 months in controlled atmosphere storage.

*Usage.*—Dual purpose, dessert and cooking.

Cold hardiness: No winter damage observed since germination of the original tree growing in Rock Island, Wash.; lowest temperature since germination approximately −20 degrees F.

Disease resistance: No distinctive resistance or susceptibility to insects or diseases prevalent in the area of origination have been noted. This cultivar has been grown only in the area of origination, near Wenatchee, Wash.

I claim:

1. A new and distinct apple tree, substantially as herein shown and described.

* * * * *